United States Patent [19]
Frankenberger, Jr. et al.

[11] Patent Number: 5,614,467
[45] Date of Patent: Mar. 25, 1997

[54] USE OF PLANT HORMONES FOR CROP IMPROVEMENT

[75] Inventors: William T. Frankenberger, Jr.; Dean A. Martens, both of Riverside, Calif.

[73] Assignee: The Regents of the University of California, Oakland, Calif.

[21] Appl. No.: 458,375

[22] Filed: Jun. 2, 1995

[51] Int. Cl.$^6$ .................................. H01N 43/38
[52] U.S. Cl. ............................ 504/138; 504/248
[58] Field of Search ................... 504/248, 138

[56] References Cited

U.S. PATENT DOCUMENTS 4,411,684 10/1983 Boyles ........................ 548/494
4,515,350 11/1983 Boyles ........................ 548/494

FOREIGN PATENT DOCUMENTS

WO94/00986 1/1994 WIPO.

OTHER PUBLICATIONS

Frankenberger, W.T., et al. (1990) "Response to *Raphanus sativus* to the auxin percursor, L–tryptophan applied to soil", *Plant and Soil* 129:235–241.

Sarwar, Muhammad, et al. (1994) "Influence of L–tryptophan and auxins applied to the rhizosphere on the vegetative growth of *Zea mays* L.", *Plant and Soil*, 160:97–104.

Sarwar, Muhammad, et al., (1992) "Tryptophan–dependent biosynthesis of auxins in soil", *Plant and Soil*, 147:207–215.

Martens, D.A., et al. (1993) "Stability of Microbial–Produced Auxins Derived From L–Tryptophan Added To Soil", *Soil Science*, 155(4):263–271.

Martens, D.A., et al. (1993) "Metabolism of Tryptophan in Soil", *Soil Biol. Biochem.* 25(12):1679–1687.

Martens, Dean, et al. (1992) "Utilization of Soil–Applied Auxins For Synchronization of Fruit Set and Yield Increase in *Citrullus lanatus*", *HortScience*, 27(6):154.

CA94:80346, Maeda et al, "Effects of various auxins on growth . . . ", Phytomorphology, 29(2) 146–55 1980.

CA66:104192, Mitchell et al, "Growth accelerating substances . . . ", J. Agric. Food Chem., 15(2), 329–33, 1967.

CA91: 135377, Popov, "Study on Optimal conditions . . . ", Fiziol. Rast. 5(2), 39–44 1979.

Primary Examiner—Richard L. Raymond
Assistant Examiner—Brian Bembenick
Attorney, Agent, or Firm—Townsend and Townsend and Crew LLP

[57] ABSTRACT

The invention provides methods and compositions for improving crop yield. The methods involve application of auxins such as indole-3-acetamide and/or tyrptamine to plants, either as a soil amendment or a foliar spray.

20 Claims, 9 Drawing Sheets

USE OF PLANT HORMONES FOR CROP IMPROVEMENT

BACKGROUND OF THE INVENTION

1. Field of the Invention

The present invention relates to methods of improving productivity of crop plants. In particular it relates to the application of compositions comprising auxins to plants.

2. Background Art

Plant hormones play an important role in controlling plant growth and development. One class of plant hormone, auxins, are known to affect a number of plant processes, such as cell division, shoot elongation, phototropic responses, and apical dominance.

Soils are known to contain compounds with auxin-like activities. These compounds are thought to be derived from microbial metabolism of various substrates. For instance, L-tryptophan has been reported to serve as precursor for the microbial formation of indole-3-acetic acid (IAA), one of the major auxin products found in soils (see, e.g., Arshad and Frankenberger *Plant Soil* 133:1–8 (1991)).

The synthesis of IAA upon application of tryptophan to soil has been shown to effect plant growth. For instance, growth of Douglas fir was increased by application of tryptophan and inoculation with a fungus capable of producing IAA from tryptophan (Frankenberger and Poth *Appl. Environ. Microbiol* 53:2908–2913 (1987)). In addition, soil-applied tryptophan as well as auxins were shown to increase growth of radish (Frankenberger et al. *Plant Soil* 129:235–242 (1990). An investigation of the influence of various levels of tryptophan and auxins such as IAA, indole-3-acetamide (IAM), and tryptophol revealed that these compounds had distinct effects on the growth of corn. In particular, the growth parameters studied there were found not to be influenced by IAM (Sarwar and Frankenberger *Plant and Soil* 160:97–104 (1994)).

The metabolism of tryptophan in soil is complex. Metabolism of tryptophan results in the formation of many products including niacin and serotonin, in addition to auxins, and is regulated by a number of microbial enzymes (see, Martens and Frankenberger *Soil Biol. Biochem.* 25:1679–1687 (1993) and FIG. 1). Recent studies indicate that the soil microbiota has more influence on auxin production than the physicochemical properties of the soil (Sarwar et al. *Plant and Soil* 147:207–215 (1992)).

A need exists for inexpensive, effective means for improving crop productivity. Means for improving productivity by providing auxins to plants in a readily available form would be particularly desirable. The present invention addresses these and other needs.

SUMMARY OF THE INVENTION

The present invention provides methods of improving productivity in crop plants by applying an effective amount of an auxin to the plants. Increased productivity can be measured by a number of parameters. For instance, the plants will typically show increased yield or synchronization of fruit set.

The auxins used in the methods of the invention are indole-3-acetamide, tryptamine or a combination thereof. The auxins can be applied according to standard methods known to those of skill in the art. For instance, the auxins may be applied at the seedling stage before transplanting the plants into a field. In this embodiment, the auxin is typically applied at a concentration of between $10^{-10}M$ and $10^{-4}M$. The auxins may also be applied to the soil with the seed and a starter fertilizer (110.88 L/ha) at a rate of about 0.024 g/hectare to about 2.4 g/hectare. Auxin addition may also be made via an irrigation dripline to the soil seedbed at a ram of about 0.036 g/hectare to about 3.6 g/hectare. The auxins may also be applied as foliar spray.

The plants used in the methods can be any crop plant. Exemplary plants include, watermelon, tomatoes and cotton.

The invention also provide compositions suitable for application to crop plants. The compositions comprise an aqueous medium and an effective amount of an auxin.

DESCRIPTION OF THE PREFERRED EMBODIMENT

Figure 1:
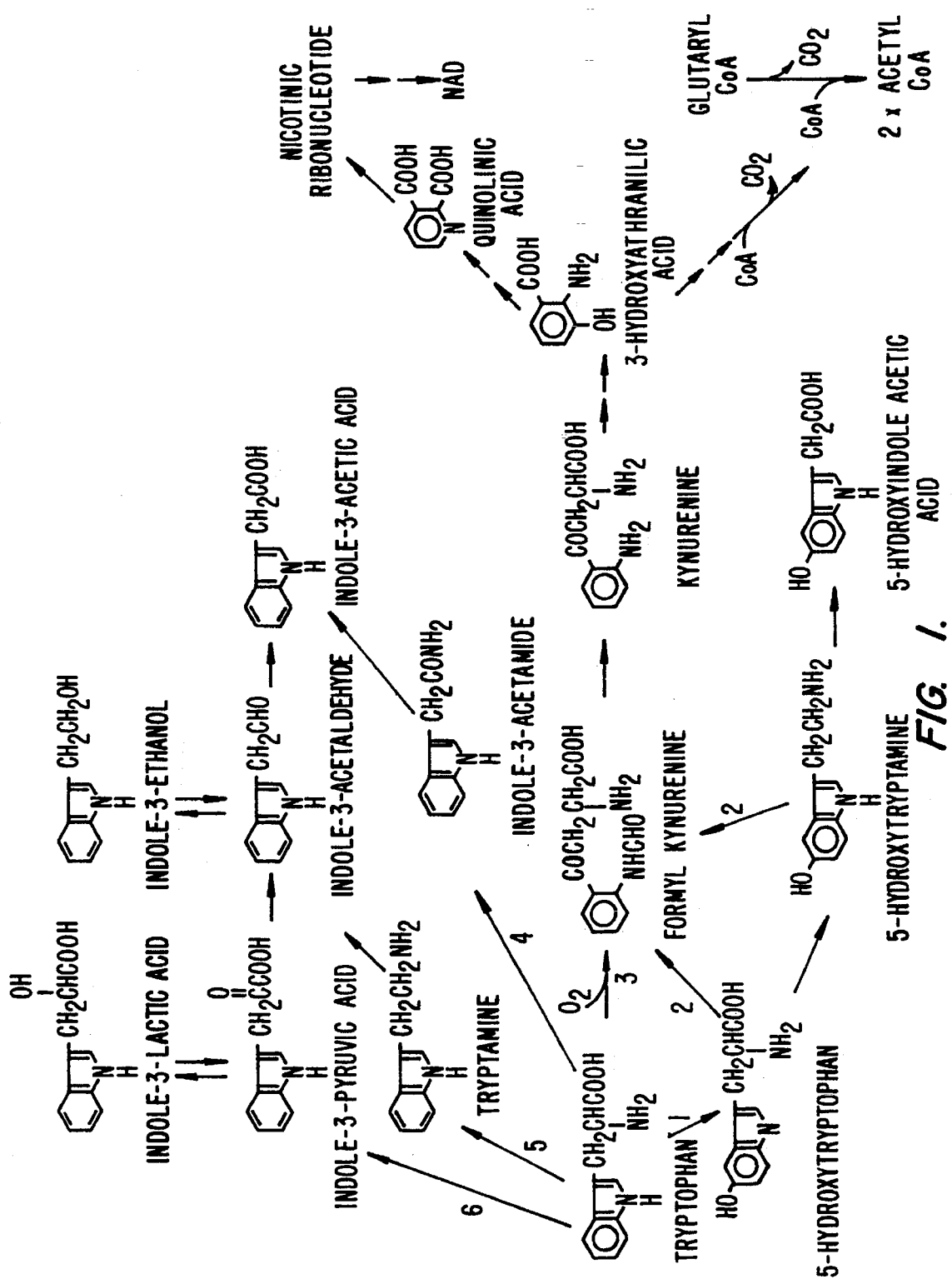
FIG. 1 shows the tryptophan metabolic pathways in bacteria. Enzymes involved in the pathways are as follows. 1. Tryptophan 5-hydroxylase; 2. Indole 2,3dioxygenase; 3. Tryptophan 2,3-dioxygenase; 4. Tryptophan decarboxylase; 6. Tryptophan aminotransferase.

The present invention relates to methods of improving crop productivity by application of auxins to the soil or to the foliage of the crop plant. As shown in detail below, two auxins, indole-3 acetamide (IAM) and tryptamine TAM), are particularly effective in improving crop productivity. In the examples below, these compounds are shown to be effective in increasing crop yield as measured in fruit weight, as well as synchronizing fruit set in plants, as measured in number of fruit per harvest.

The compounds of the invention may be applied to the soil or to plants according to well known methods. The auxins may be applied alone or in mixture with other plant hormones, fertilizers, pesticides or fungicides. The compositions may be applied in a mixture with a carrier or, if necessary, other auxiliary agents to form any one of the standard types of preparations commonly used in agriculture;, for example, a dry blend, granules, a wettable powder, an emulsion, an aqueous solution and the like.

Suitable solid carriers are clay, talc, kaolin, bentonite, terra abla, calcium carbonate, diatomaceous earth, silica, synthetic calcium silicate kieselguhr, dolomite, powdered magnesia, Fuller's earth, gypsum and the like. Solid compositions may also be in the form of dispersible powders or grains, comprising, in addition to the auxins, a suffactant to facilitate the dispersion of the powder or grains in liquid.

Liquid compositions include solutions, dispersions or emulsions containing the auxins together with one or more surface-active agents such as wetting agents, dispersing agents, emulsifying agents, or suspending agents. In those applications in which the compounds are applied as a foliar spray, surface active agents are preferably used.

Surface-active agents may be of the cationic, anionic, or non-ionic detergents. Suitable agents include, for example, quaternary ammonium compounds; non-ionic detergents such as polyoxyethylene 9 lauryl ether, octoxynol 9, and the like; and ionic detergents such as sodium dodecyl sulfate and the like.

Suitable suspending agents are, for example, hydrophilic colloids, for example polyvinylpyrrollidone and sodium carboxymethylcellulose, and the vegetable gums, for example gum acacia and gum tragacanth.

Aqueous solutions, dispersions or emulsions may be prepared by dissolving the auxins in water or an organic solvent which may, if desired, contain one or more wetting, dispersing, or emulsifying agents. Suitable organic solvents are methanol, isopropylalcohol, propylene glycol, diacetone alcohol, and mineral oil.

The auxins may also be formulated by microencapsulation. Microcapsules containing the desired auxin may be prepared by co-acervation; or, more preferably, by stirred interfacial polymerization of (for example) an isocyanate/diamine system. The resulting microcapsules may be used as an aqueous suspension.

The compositions which are to be used in the form of aqueous solutions, dispersions or emulsions are generally supplied in the form of a concentrate containing a high proportion of the auxins, and the concentrate is then diluted with water before use. These concentrates are usually required to withstand storage for prolonged periods and after such storage, to be capable of dilution with water in order to form aqueous preparations which remain homogeneous for a sufficient time to enable them to be applied by conventional spray equipment. In general, concentrates may conveniently contain from 10–60 percent by weight of the auxins. Dilute preparations ready for use may contain varying amounts of the auxins, depending upon the purpose for which they are to be used, and a dilute preparation containing between 0.01 and 10.0 percent and preferably 0.01 and 1 percent, by weight of the auxins may normally be used.

In carrying out the methods of the invention, an "effective mount" of the auxins are applied to the plants. As defined here, an "effective amount" is an mount sufficient to increase crop productivity. Crop productivity can be determined by, for example, measuring increased yield (e.g., as measured by total weight of the desired plant organ, such as fruit, roots, tubers, and the like), increased synchronization of fruit set, or other parameters commonly used to measure productivity of a crop plant.

One of skill will recognize that an effective amount of auaxin will depend upon a number of factors, for example, the particular formulation selected for use, whether the compound is to be applied for foliage or root uptake, the effect desired, and the plant species whose growth is to be regulated. For instance, the compositions of the invention can be applied as a soil drench at the seedling stage before plants are transplanted to the field. In these embodiments, the auxins are applied at a concentration of between about $10^{-10}$M and about $10^{-4}$M to the seedlings about one to two weeks before transplanting. Concentrations between about $10^{-9}$M and about $10^{-6}$M are typically used.

When applying the compositions to plants in the field, an, application rate of from about 0.024 g to about 10 g per hectare is suitable, typically between about 0. 1 g to about 5.9 g per hectare, while from about 2.4 g to about 3.6 g per hectare is preferred for most purposes. In foliar sprays, the compositions of this invention can be applied in a range of about 2 to about 25 ppm. A preferred range is between 5 to 10 ppm. Foliar spray is most effective when applied soon after seedling emergence and again just at appearance of first flowers. In the case of melons the second applicatic,n should be at the appearance of female flowers. In all cases routine tests are necessary to determine the best rate of application of a specific formulation for any specific purpose for which it is suitable.

The compositions and methods of the invention can be used on a wide variety of plants. Exemplary plants include species from the genera Asparagus, Atropa, Avena, Brassica, Citrus, Citrullus, Capsicum, Cucumis, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Panieum, Persea, Pisum, Pyrus, Prunus, Raphanus, Secale, Senecio, Sinapis, Solanum, Sorghum, Trigonella, Triticum, Vigna, and, Zea.

The methods of the invention can be used in a variety of conditions and environments. For instance, the compositions of the invention can be used as soil amendments in virtually any type of soil. Since the conversion of auxins applied to the soils is primarily a biological phenomenon, the physical characteristics of the soils is not critical to the invention.

EXAMPLES

The application of naturally-occurring plant growth hormones, IAM or TAM as soil amendments was found in field studies to synchronize harvest dates and concomitantly increase yields of watermelon (Citrullus lanatus) var. 'Tiffany' and 'Picnic' when applied at the seedling stage. Optimum auxin concentrations from $10^{-6}$M to $10^{-9}$M of IAM or TAM applied to the seedling stage one week before transplanting into the field synchronized maturity of the subsequent melon production and increased the number of harvested melons for the 'Tiffany' melon and increased harvested weight and melon number for the 'Picnic' melon. A one time application of IAM or TAM at $10^{-6}$ to $10^{-9}$M resulted in a very economical management option for increasing production as well as reducing labor costs associated with vegetable and fruit production.

LABORATORY STUDIES

Soil application of the plant auxins, IAM and TAM and their subsequent microbial transformations resulting in the synthesis of IAA in the root zone of watermelons (seedless var. 'Tiffany' and seed var. 'Picnic') resulted in increased yield and synchronization of melon maturity. The auxins, IAM and TAM were identified in bench-scale laboratory studies to have a long soil residence time measured as $t^{1/2}$ (half-life) of 127 h and 109 h, respectively, compared with the half-life of 38 h for IAA (average of six soils surveyed). In addition, approximately 20% of the applied IAM and TAM was found to be transformed into IAA after incubation for 5 days in soil (data not shown). These auxins are not partitioned or held by the soil consituents, and can therefore be leached from the root zone or rootball if irrigation is not carefully managed during the first week of application.

FIELD STUDY

Experimental Design

Watermelon seedling transplant plugs (5 g potting soil mix) were treated with 3 ml of solution as a soil drench containing $10^{-4}$M (3200 µg/g soil) to $10^{-10}$M (0.0032 µg/g soil) IAM or TAM one week before transplanting into a Buren fine sandy loam soil (mixed, thermic Haplic Durixeralf). The experimental design was a randomized complete block replicated 10 times. Fertilization was applied as a preplant and also drip irrigation side dressings with manual weed control.

Three harvests were conducted for the seedless and seed watermelon varieties and the results are summarized in Tables 1 and 2.

Results 'Tiffany' seedless melons

Harvest 1. The addition of two auxins increased 'Tiffany' harvested weight (average of $10^{-4}$M to $10^{-10}$M treatments) by 31% (19 kg) and 49% (30.0 kg) for IAM and TAM, respectively, over the control plants (61.3 kg). The optimum application levels of IAM ($10^{-9}$M) and TAM ($10^{-6}$M) increased harvested weight by 79% (48.4 kg) and 106% (65 kg), respectively, compared with the control plants. The number of melons harvested at the first picking was increased by an average of 33% (4 melons) and 54% (6.5 melons) for the IAM and TAM treatments, respectively, compared with the controls (12 melons). The optimum application levels of IAM ($10^{-9}$M) and TAM ($10^{-5}$M) increased melon numbers at the first harvest by 75% (9 melons) and 108% (13 melons), respectively.

Harvest 2. Measured weights (average of $10^{-4}$M to $10^{-10}$M treatments) were increased 40% (27.6 kg) and 26% (18 kg) by application of IAM and TAM, respectively, compared with the control plants (69.1 kg). Optimum levels of IAM ($10^{-9}$M) and TAM ($10^{-4}$M) increased the melon weight by 82% (56.6 kg) and 58% (40.1 kg), respectively. The number of melons harvested at the second picking was increased 64% (8.3 melons) and 50% (6.5 melons) for the IAM and TAM treatments, respectively, compared with the control plants (13 melons). The optimum concentrations for IAM ($10^{-9}$M) and TAM ($10^{-4}$M) increased the number of melons 108% (14 melons) and 92% (12 melons), respectively, when compared with control plants.

Harvest 3. The third harvest resulted in less melon production with the treated plants compared with the control plants due to the synchronization effect noted for the first two harvests.

For the three harvests, the optimum application level for IAM ($10^{-9}$M) and TAM ($10^{-6}$M) increased the weight of harvested watermelons 52% and 35% and number of melons 54% and 35%, respectively, when compared with the control plants. This results in a yield increase of 9.4 kg melon and 6.2 kg melon plant$^{-1}$ and an increase in the number of harvested melons by 2.0 and 1.3 plant$^{-1}$ for the two levels, respectively, when compared with the nontreated control plants.

Soil auxin applications promoted a synchronization of the watermelon harvest. Application of the optimum levels of IAM ($10^{-9}$M) and TAM ($10^{-6}$M) increased the weight of watermelons 81% and 72% for the first two harvests, respectively. The two treatments resulted in 86% and 92% of the total melon weight to be ready at a single possible harvest (average date between the 6-day harvest interval) when compared with 70% for the control plants.

'Picnic' seed melons

Harvest 1. Soil application of IAM and TAM increased harvested 'Picnic' melon weight (average of $10^{-4}$M to $10^{-10}$M) by 150% (21.2 kg) and 120% (16.9 kg) for IAM and TAM, respectively, over the control plants (14.1 kg). The optimum application levels for IAM ($10^{-6}$M) and TAM ($10^{-7}$M) increased harvested melon weight 230% (32.9 kg) and 328% (46.2 kg), respectively, over the controls. Optimum rates of IAM ($10^{-6}$M) and TAM ($10^{-7}$M) increased the number of melons by 200% (4 melons) and 250% (5 melons), respectively, over the controls (2 melons).

Harvest 2. Melon weights (average of 7 treatments) increased by 14% (7.7 kg) and 0.4% (2.2 kg) when treated with IAM and TAM, respectively, compared with the control plants (55 kg). The optimum treatments (IAM, $10^{-8}$M and TAM, $10^{-9}$M) increased melon weight by 37% (20.4 kg) and 82% (45.1 kg), respectively. The optimum rates of IAM ($10^{-6}$M) and TAM ($10^{-9}$M) increased the second harvest melon numbers by 50% (4 melons) and 89% (7 melons), respectively, when compared with the control melons (8 melons).

Harvest 3. Melon weights were increased by 86% (56.7 kg) (IAM, $10^{-5}$M) and 40% (27.8 kg) (TAM, $10^{-9}$M) when compared to the nontreated control plants (69.4 kg). An increase in number of melons harvested of 67% (8 melons) (IAM, $10^{-5}$M and 33 9 (4 melons) (TAM, $10^{-10}$M) was also noted when compared with the control (12 melons).

For the three harvests, the optimum application rates increased total harvest weight of 'Picnic' melons by 76% (IAM, $10^{-5}$M) and 73% (TAM, $10^{-9}$M) and total number of melons by 68% (IAM, $10^{-5}$M) and 59% (TAM, $10^{-9}$M) over the control. The optimum application rates (IAM, $10^{-5}$M and TAM, $10^{-9}$M) resulted in an additional 10.5 kg. and 10.1 kg, respectively, of melons harvested and increased the number of harvested melons by 1.5 and 1.3 melons plant$^{-1}$, respectively, when compared with the control plants.

STATISTICAL ANALYSIS

'Tiffany' seedless melons

Figure 2:
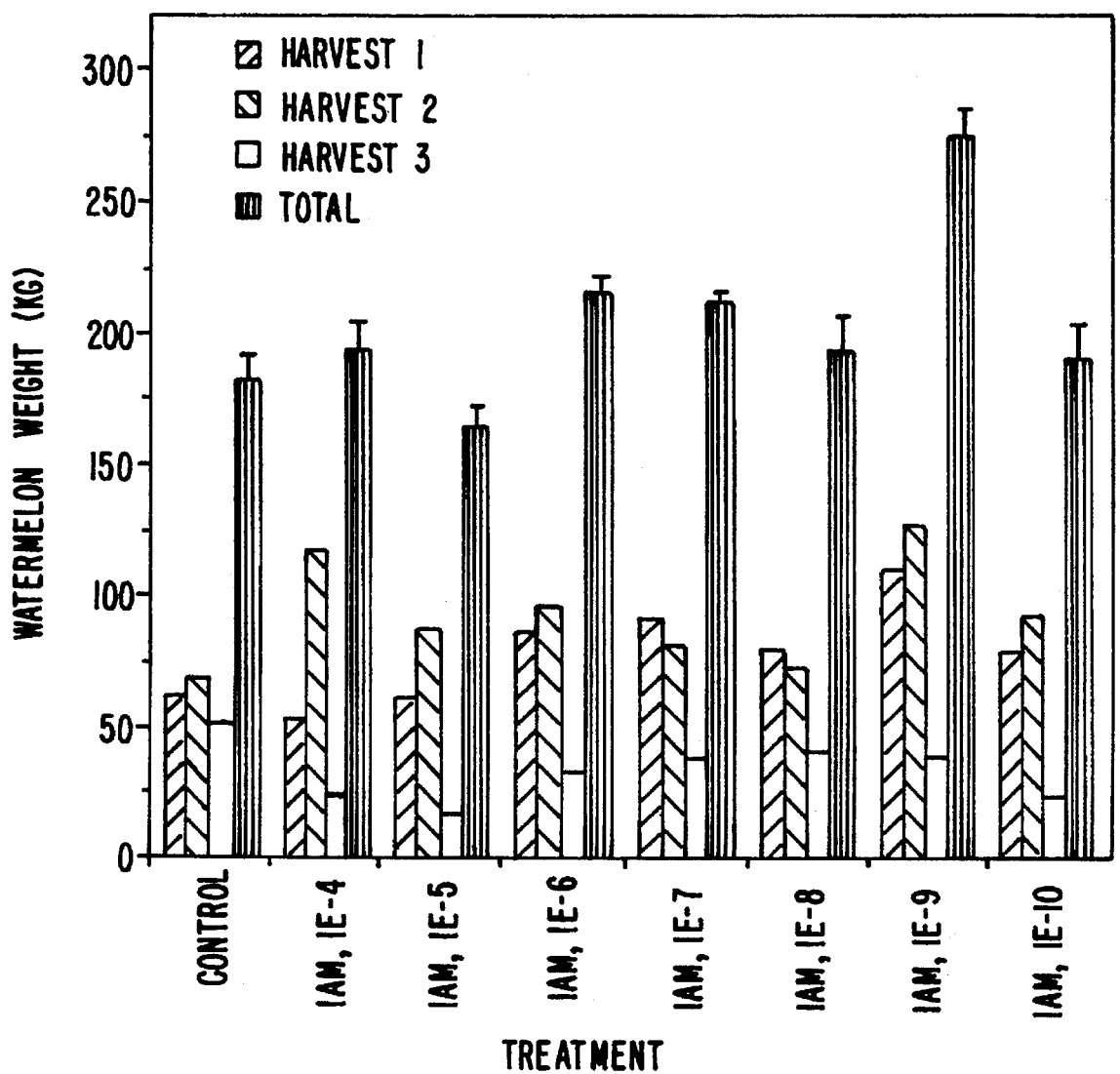
FIG. 2 shows response of "Tiffany" melon yield (kg) to applications of IAM ($10^{-4}M$ to $10^{-10}M$).
Figure 3:
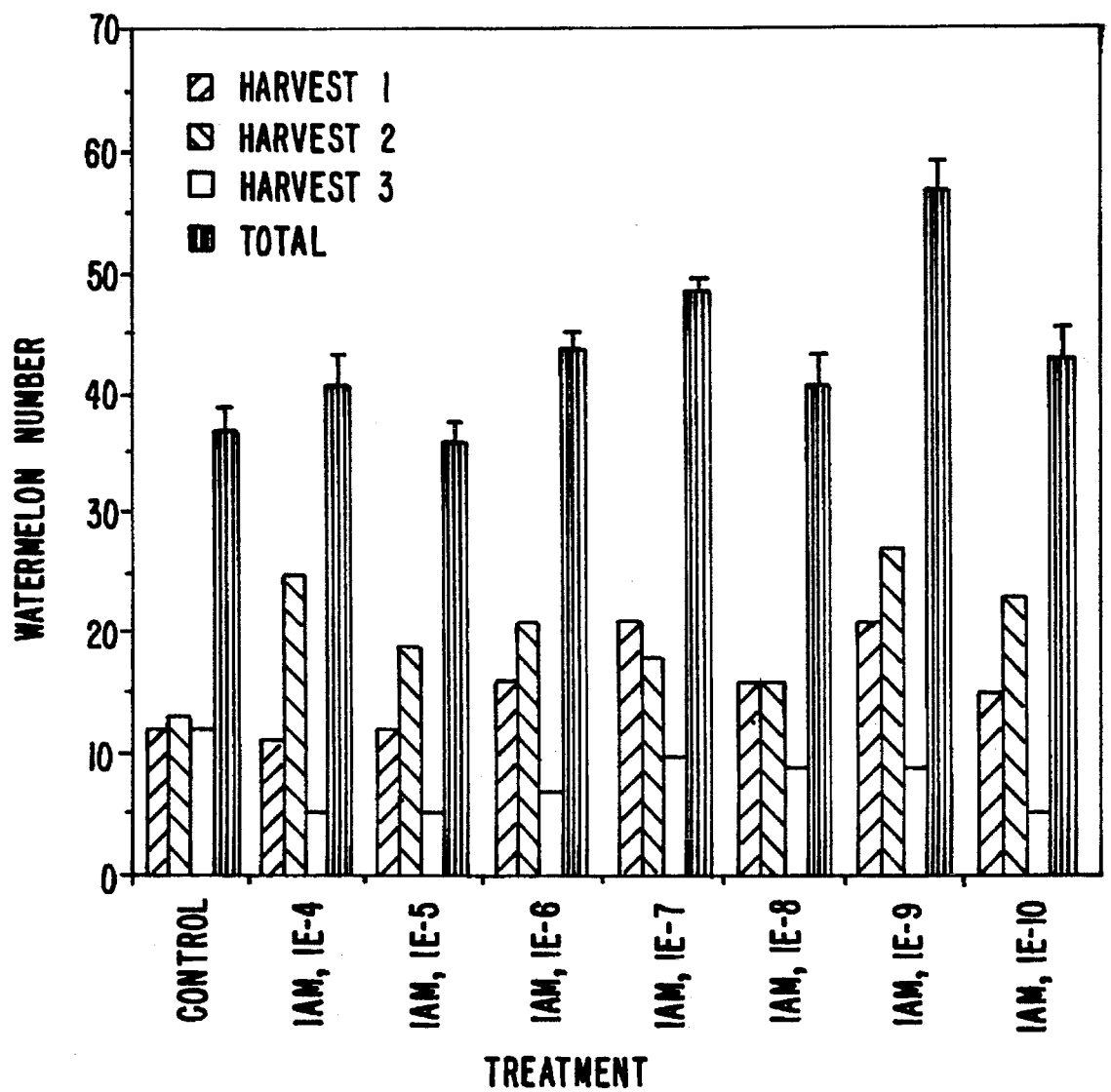
FIG. 3 shows response of "Tiffany" melon yield (number of fruit) to applications of IAM ($10^{-4}M$ to $10^{-10}M$).
Figure 4:
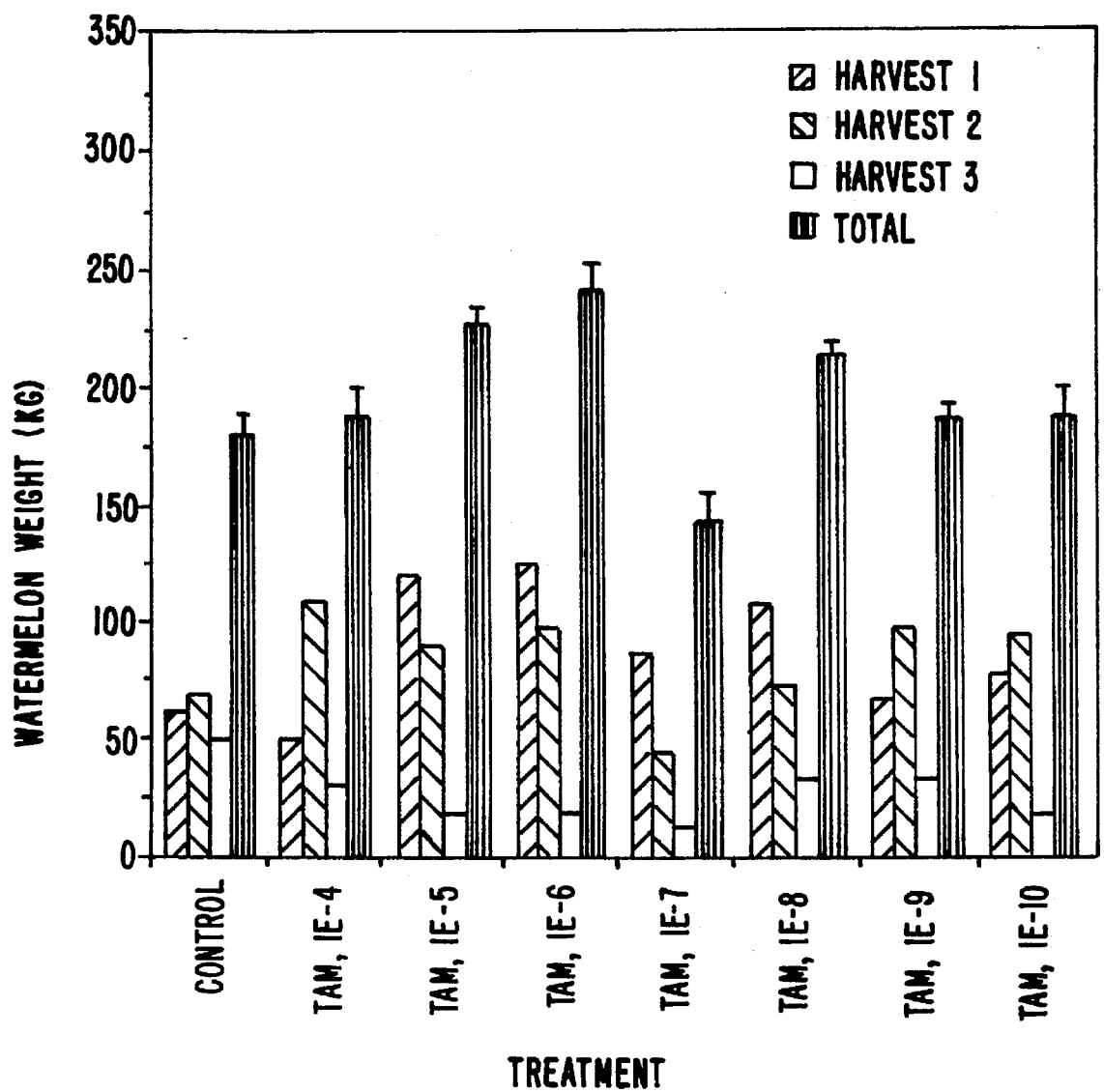
FIG. 4 shows response of "Tiffany" melon yield (kg) to applications of TAM ($10^{-4}M$ to $10^{-10}M$).
Figure 5:
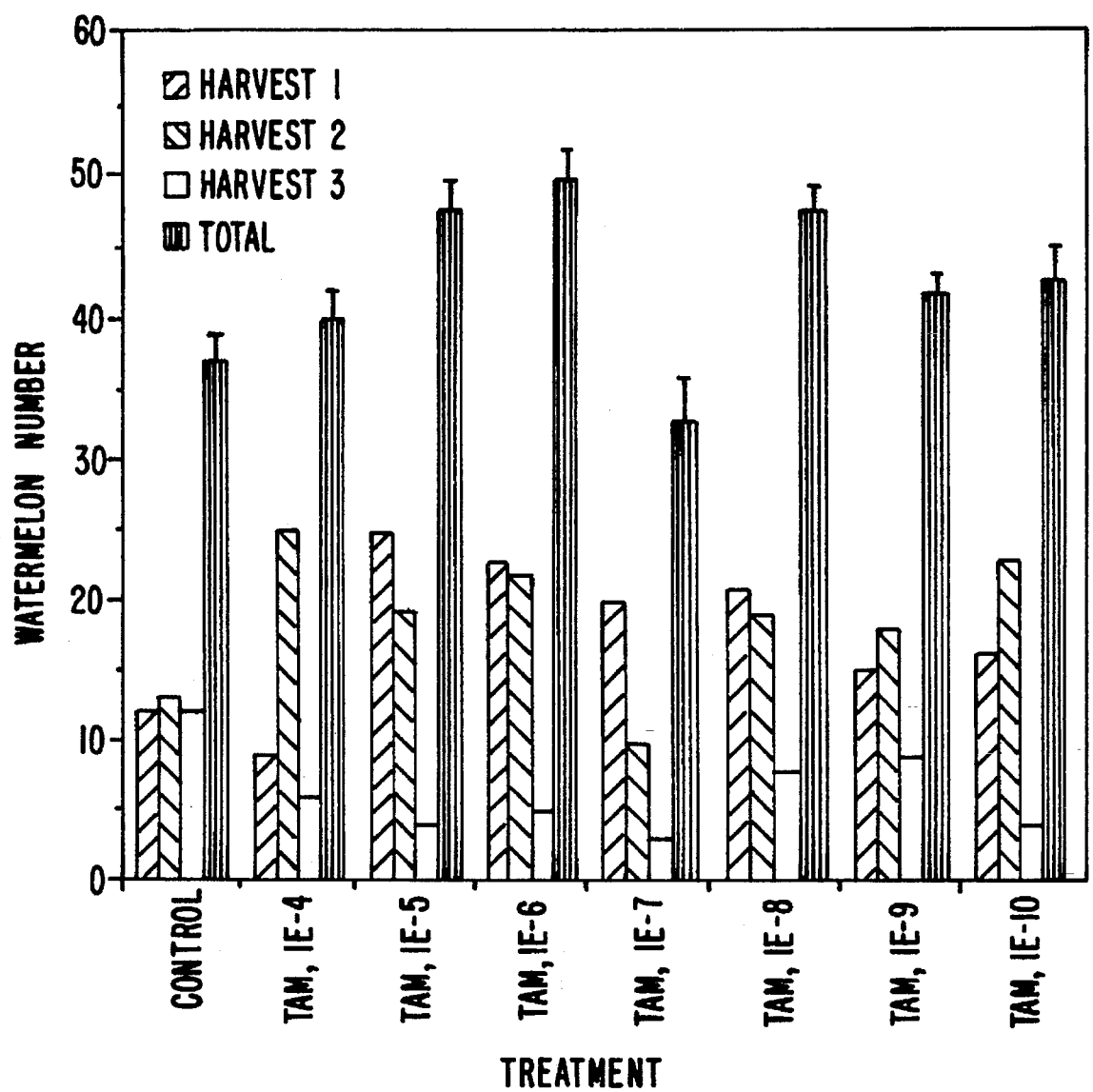
FIG. 5 shows response of "Tiffany" melon yield (number of fruit) to applications of TAM ($10^{-4}M$ to $10^{-10}M$).

Application of IAM and TAM at concentrations ranging from $10^{-4}$M to $10^{-10}$M resulted in a general dose response curve for melon weight and number (FIGS. 2–5). Statistical analyses indicated that the Harvest 1 and 2 weight and number of melons were significantly different from Harvest 3 data at the 0.01% level. Harvest 1 and 2 weight and number of melons were significantly correlated with total harvested weight (r=0.96*) and melon number (r=0.91*). This suggests a synchronized harvest response for Harvest 1 and 2 due to the IAM and TAM applications. Addition of TAM at $10^{-5}$M and $10^{-6}$M and IAM at $10^{-9}$M significantly (5% level) increased melon weight with 8.0, 9.5 and 10.6 kg of melon plant$^{-1}$ for the first two harvests, respectively, compared with the control plants. Over the three harvest dates, IAM ($10^{-9}$M) significantly (5% level) increased melon yield when compared to the, control plants (130.4 kg melon plant$^{-1}$). The standard deviations determined for the treated plants vs. the control plants showed no significant differences, suggesting that the treated plants yielded a similar variation of melon sizes as the controls. Some treatments resulted in a lower standard deviation for melon weight and number of melons suggesting that the yield-enhancing treatments also resulted in an increased uniformity of melon weight between plants Table 1). The application of IAM and TAM did not significantly increase the weight of the melons but significantly increased the ability of the plant to support additional melons. Growth parameters such as plant size and number of branches measured 3 weeks after transplanting were not significantly correlated to the resulting yield suggesting that the plants would not require additional space. The treatments did decrease the time period to the first bloom by 7–10 days when compared with the control plants.

'Picnic' seed melons

Figure 6:
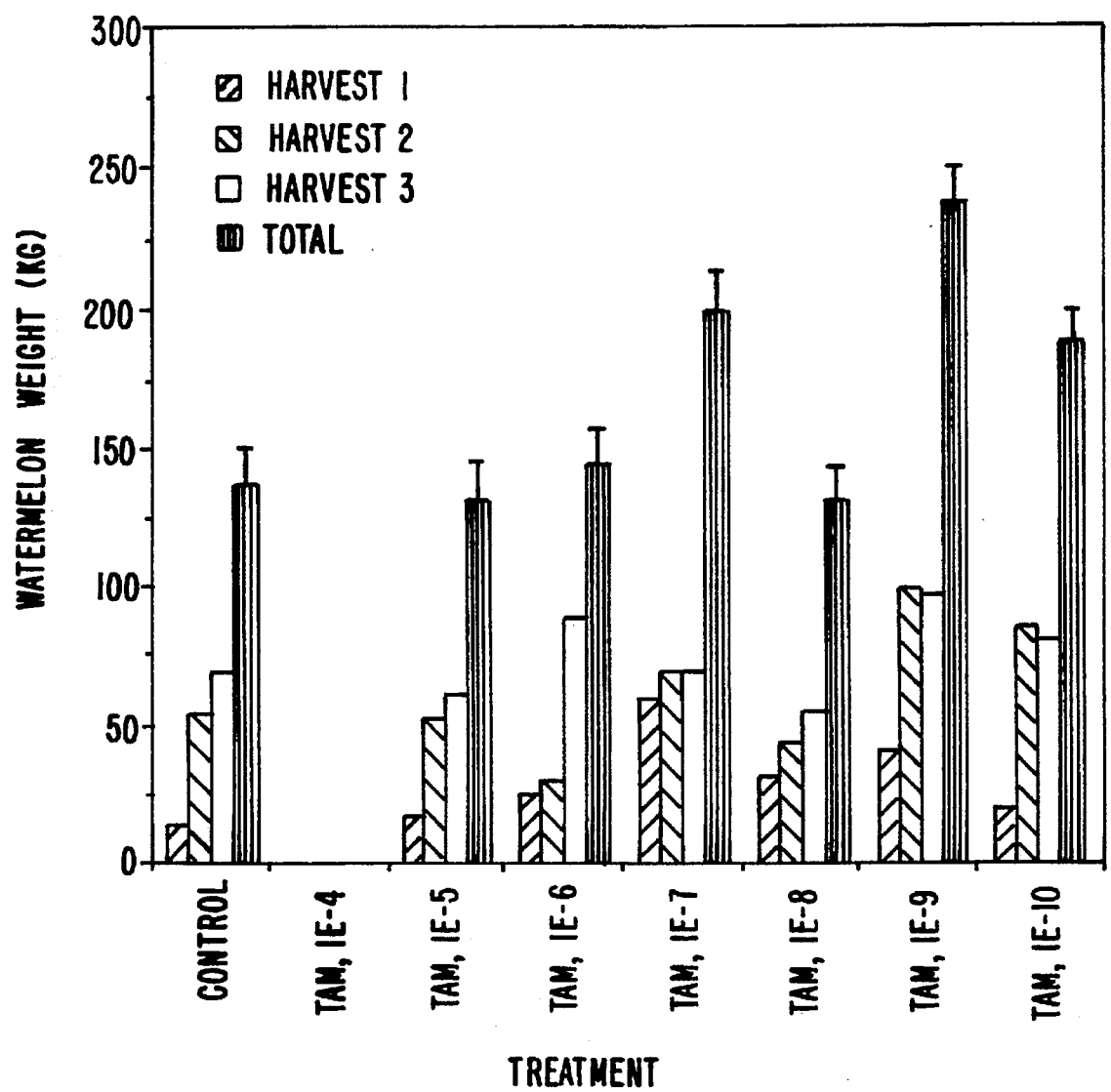
FIG. 6 shows response of "Picnic" melon yield (kg) to applications of IAM ($10^{-4}M$ to $10^{-10}M$).
Figure 7:
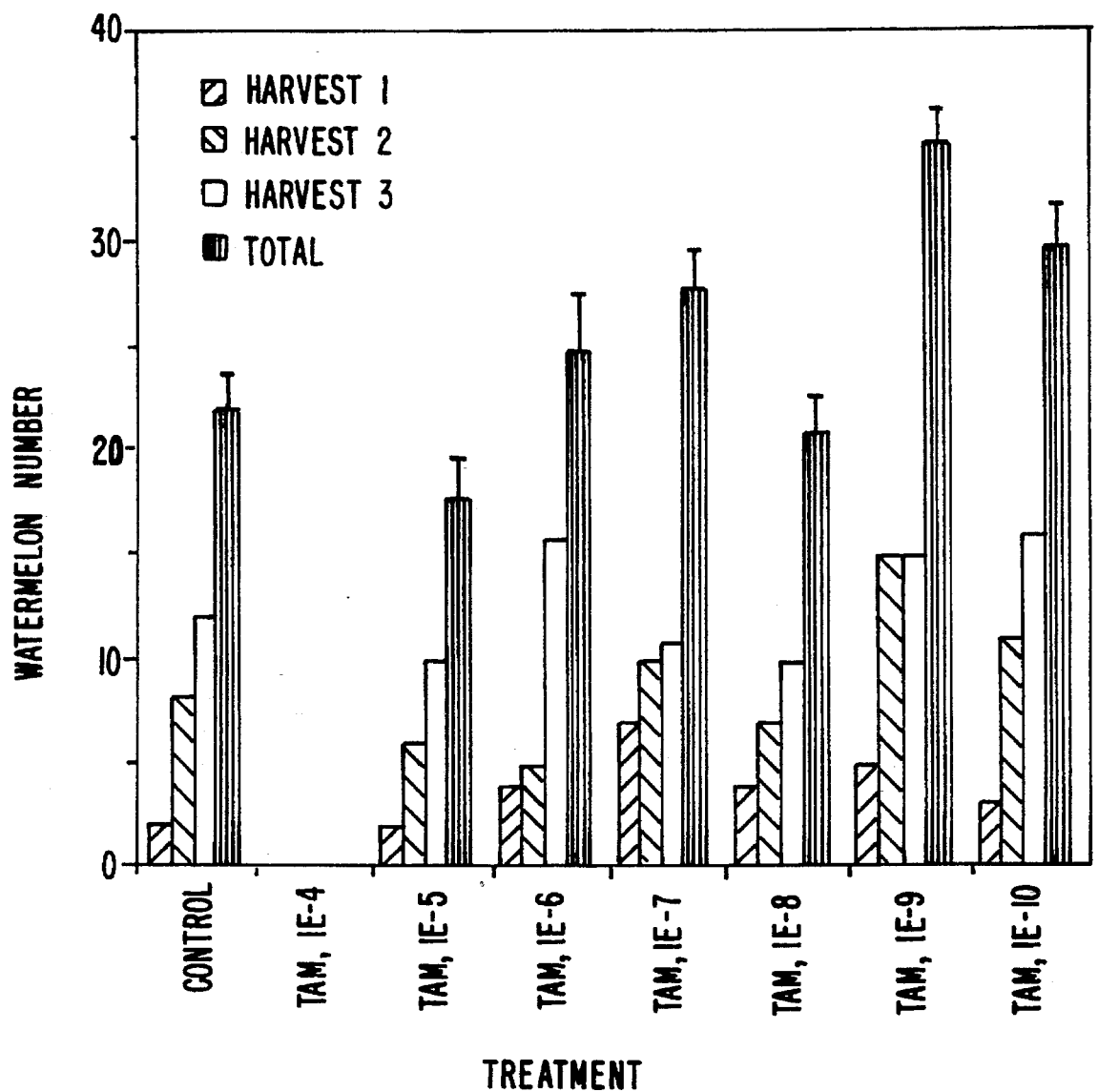
FIG. 7 shows response of "Picnic" melon yield (number of fruit) to applications of IAM ($10^{-4}M$ to $10^{-10}M$).
Figure 8:
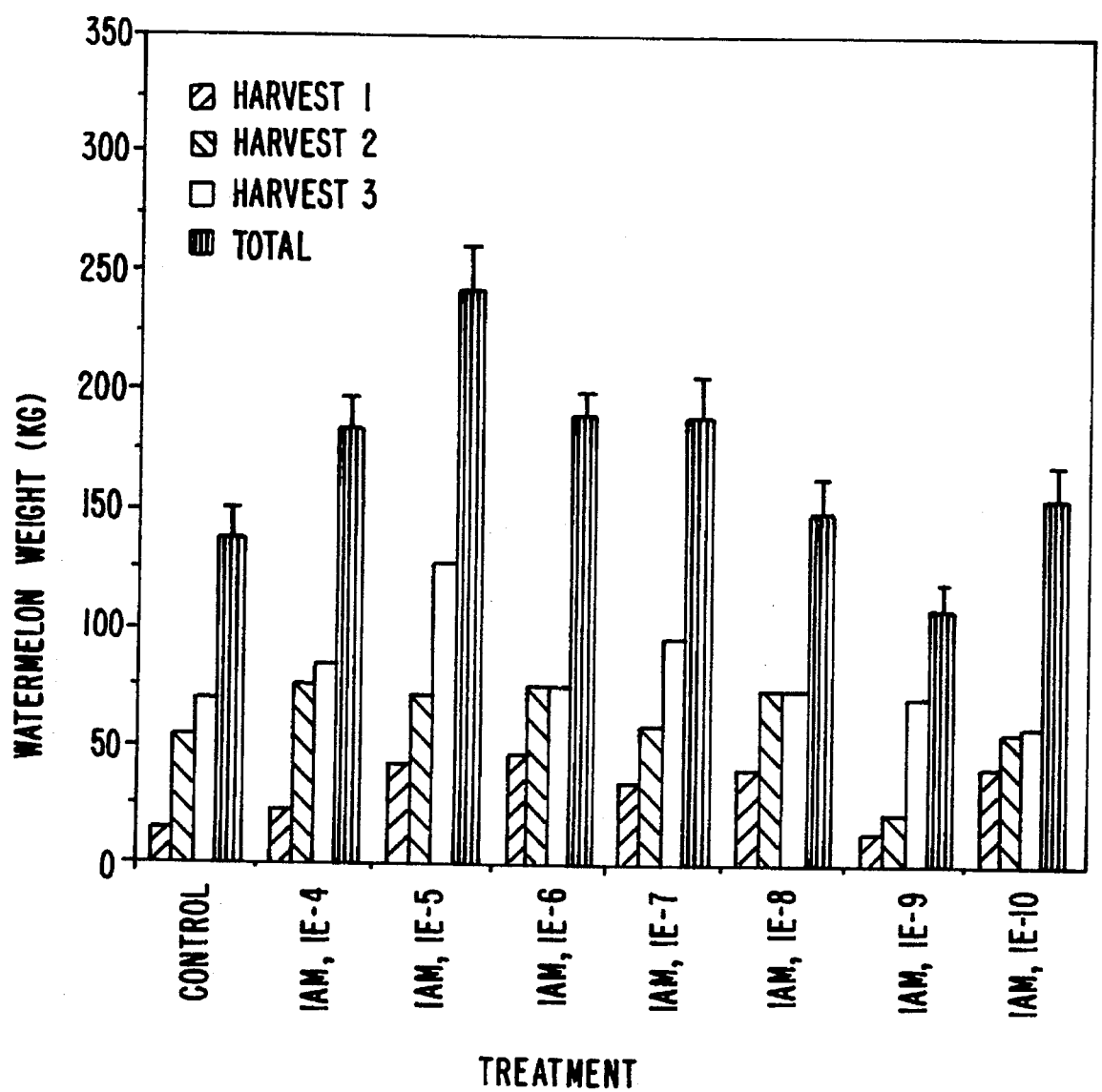
FIG. 8 shows response of "Picnic" melon yield (kg) to applications of TAM ($10^{-4}M$ to $10^{-10}M$).
Figure 9:
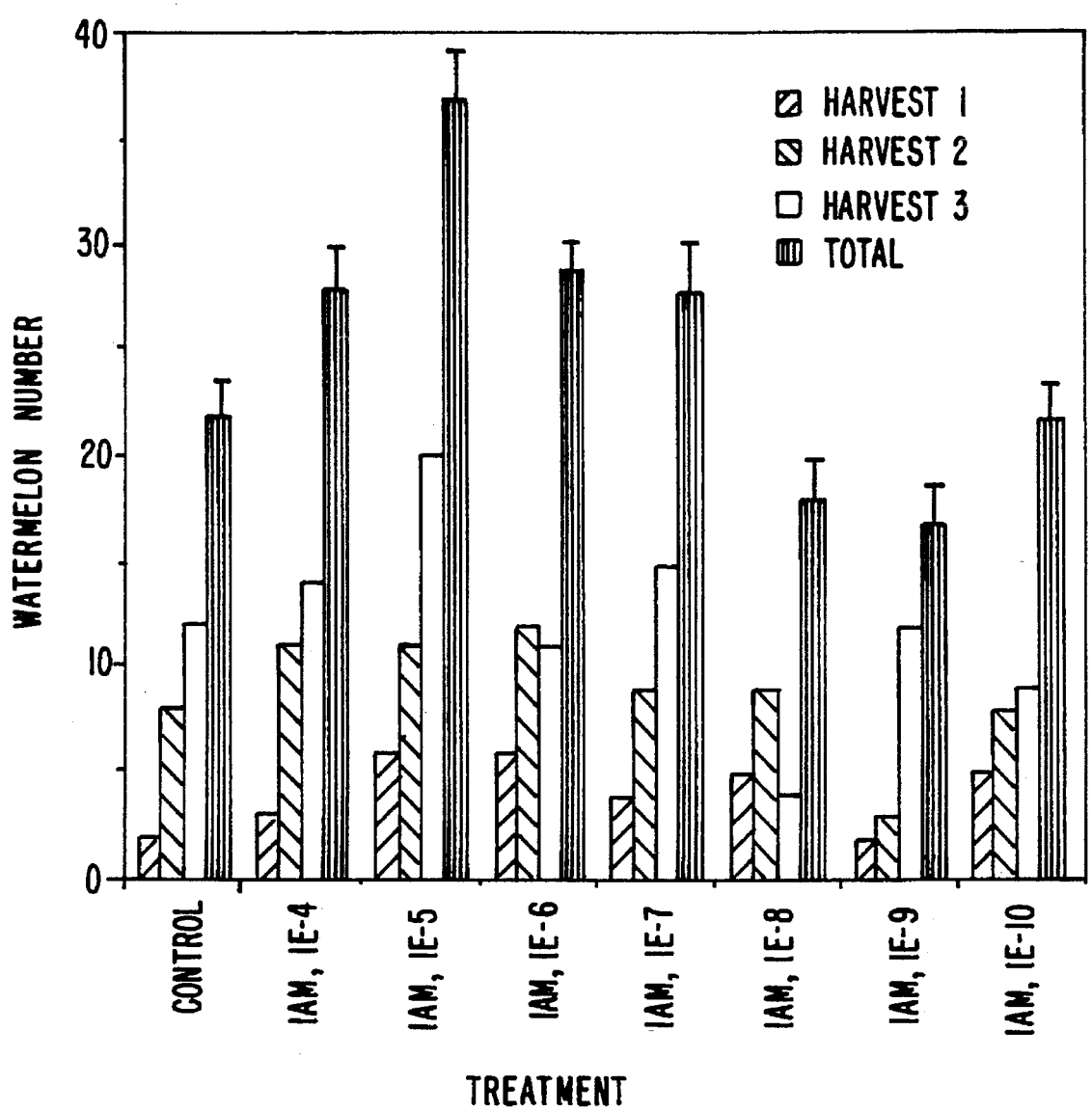
FIG. 9 shows response of "Picnic" melon yield (number of fruit) to applications of TAM ($10^{-4}M$ to $10^{-10}M$).

Application of IAM and TAM ($10^{-4}$M to $10^{-10}$M rates) affected the yield of melons differently than the effect of IAM and TAM on seedless 'Tiffany' melons (FIGS. 6–9). The seed melons matured later than seedless melons. Harvests 2 and 3 weight and number for the seed melons were significantly different (0.01% level) from Harvest 1. The synchronization effect was noted at Harvests 2 and 3 with total weight significantly correlated (r=0.95***) with total harvested weight. A significant (5% level) increase in the melon weight plant$^{-1}$ was observed with the application of optimum levels of IAM (10.5 kg, $10^{-5}$M; 5.4 kg, $10^{-7}$M) and TAM (6.2 kg, $10^{-7}$M) compared with the controls (13.9 kg). In addition, IAM ($10^{-5}$M) and TAM ($10^{-9}$M) significantly (5% level) increased the number of harvested melons 68% and 59%, respectively, when compared with the control plants. As noted for the seedless melons, the standard deviations for the weight and number of melons harvested was not significantly different from the control plants. Additions of IAM and TAM to the seedling growth stage of the 'Picnic' melons significantly increased both weight of the melons and number of melons harvested. Growth parameters such as plant size and number of branches measured 3 weeks after transplanting were not significantly correlated to resulting yield. The treatments did not have an effect on, early flowering when compared with the control plants.

TABLE 1

Cumulative yield of "Tiffany" watermelon in response to auxins during three harvests

| Treatment | Harvest 1 | | Harvest 2 | | Harvest 3 | | Total† | |
|---|---|---|---|---|---|---|---|---|
| | Weight | No. of melons | Weight | No. of melons | Weight | No. of melons | Weight | No. of melons |
| Control | 61.3 | 12 | 69.1 | 13 | 50.1 | 12 | 180.5 (9.4) | 31 (1.7) |
| IAM, $10^{-4}$ | 53.3 | 11 | 116.6 | 25 | 23.4 | 5 | 193.3 (9.7) | 41 (2.3) |
| IAM, $10^{-5}$ | 61.1 | 12 | 87.6 | 19 | 15.7 | 5 | 164.4 (7.4) | 36 (1.6) |
| IAM, $10^{-6}$ | 86.9 | 16 | 96.8 | 21 | 32.4 | 7 | 216.1 (6.6) | 44 (1.6) |
| IAM, $10^{-7}$ | 91.8 | 21 | 82.8 | 18 | 38.3 | 10 | 212.9 (4.9) | 49 (1.2) |
| IAM, $10^{-8}$ | 80.3 | 16 | 73.1 | 16 | 39.8 | 9 | 193.2 (13.3) | 41 (2.6) |
| IAM, $10^{-9}$ | 110.1 | 21 | 126.3 | 27 | 38.2 | 9 | 274.6 (9.7) | 57 (2.1) |
| IAM, $10^{-10}$ | 87.8 | 15 | 91.5 | 23 | 22 | 5 | 191.3 (12.3) | 43 (2.1) |
| TAM, $10^{-4}$ | 49.5 | 9 | 109.2 | 25 | 29.8 | 6 | 188.5 (11.6) | 40 (2.1) |
| TAM, $10^{-5}$ | 120.4 | 25 | 90.9 | 19 | 17.3 | 4 | 228.6 (8.1) | 48 (1.9) |
| TAM, $10^{-6}$ | 126.4 | 23 | 98.5 | 22 | 18.1 | 5 | 243 (11.2) | 50 (2.2) |
| TAM, $10^{-7}$ | 87.1 | 20 | 45.7 | 10 | 12.2 | 3 | 145 (13.2) | 33 (2.9) |
| TAM, $10^{-8}$ | 109 | 21 | 74.1 | 19 | 34 | 8 | 217.1 (5.7) | 48 (1.5) |
| TAM, $10^{-9}$ | 67.4 | 15 | 98.1 | 18 | 32.3 | 9 | 188.8 (7.4) | 42 (1.5) |
| TAM, $10^{-10}$ | 77.6 | 16 | 95.3 | 23 | 17.1 | 4 | 190 (12.3) | 43 (2.6) |

†Value in parentheses indicates standard deviation for the respective treatment.

TABLE 2

Cumulative yield of "Picnic" watermelon in response to auxins during three harvests

| Treatment | Harvest 1 | | Harvest 2 | | Harvest 3 | | Total† | |
|---|---|---|---|---|---|---|---|---|
| | Weight | No. of melons | Weight | No. of melons | Weight | No. of melons | Weight | No. of melons |
| Control | 14.1 | 2 | 55 | 8 | 69.4 | 1 | 138.5 (13.4) | 22 (2.1) |
| IAM, $10^{-4}$ | 22.9 | 3 | 76 | 11 | 85.2 | 14 | 184.1 (13.3) | 28 (2.1) |
| IAM, $10^{-5}$ | 43.1 | 6 | 71.6 | 11 | 128.8 | 20 | 243.5 (17.6) | 37 (2.5) |
| IAM, $10^{-6}$ | 47 | 6 | 76 | 12 | 68.6 | 11 | 191.6 (9.4) | 29 (1.4) |
| IAM, $10^{-7}$ | 35.4 | 4 | 60 | 9 | 97.5 | 15 | 192.9 (17.7) | 28 (2.5) |
| IAM, $10^{-8}$ | 41.6 | 5 | 75.4 | 9 | 33.7 | 4 | 150.7 (17.4) | 18 (2.0) |
| IAM, $10^{-9}$ | 14.6 | 2 | 21.5 | 3 | 72.3 | 12 | 108.4 (11.5) | 17 (1.8) |
| IAM, $10^{-10}$ | 41.6 | 5 | 56.9 | 8 | 59.6 | 9 | 158.1 (12.0) | 22 (1.8) |
| TAM, $10^{-4}$ | 0 | 0 | 0 | 0 | 0 | 0 | 0 | 0 |
| TAM, $10^{-5}$ | 36.4 | 2 | 53.6 | 6 | 62.7 | 10 | 132.7 (15.9) | 18 (2.2) |
| TAM, $10^{-6}$ | 25.4 | 4 | 31.9 | 5 | 89.1 | 16 | 146.4 (14.9) | 25 (2.8) |
| TAM, $10^{-7}$ | 60.3 | 7 | 70.2 | 10 | 70.2 | 11 | 200.7 (14.1) | 28 (2.2) |
| TAM, $10^{-8}$ | 32.3 | 4 | 44.4 | 7 | 56.9 | 10 | 133.6 (12.4) | 21 (2.0) |
| TAM, $10^{-9}$ | 41.6 | 5 | 100.3 | 15 | 97.5 | 15 | 239.4 (11.8) | 35 (1.6) |
| TAM, $10^{-10}$ | 20.6 | 3 | 86.1 | 11 | 81.9 | 16 | 188.6 (11.3) | 30 (1.9) |

†Value in parentheses indicates standard deviation for the respective treatment.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method of improving productivity in a crop plant, the method comprising applying an effective amount of an auxin selected from the group consisting of indole-3-acetamide, tryptamine and a combination thereof.

2. The method of claim 1, wherein the auxin is applied at the seedling stage before transplanting the plants into a field.

3. The method of claim 2, wherein the auxin is applied at a concentration of between $10^{-9}$M and $10^{-6}$M.

4. The method of claim 1, wherein the auxin is applied to the soil.

5. The method of claim 4, wherein the auxin is applied at a rate of about 0.024 g/hectare to about 2.41 g/hectare.

6. The method of 1, wherein the auxin is indole-3-acetamide.

7. The method of 1, wherein the auxin is tryptamine.

8. The method of claim 1, wherein the auxin is applied to the foliage of the plant.

9. The method of claim 1, wherein the plant is watermelon.

10. The method of claim 1, wherein improved productivity is measured as increased total yield.

11. The method of claim 1, wherein improved productivity is measured as synchronization of fruit set in the plants.

12. A method of increasing yield in a melon plant, the method comprising applying an effective amount of an auxin selected from the group consisting of indole-3-acetamide, tryptamine and a combination thereof.

13. The method of claim 12, wherein the auxin is applied to the plant at the seedling stage.

14. The method of claim 13, wherein the auxin is applied at a concentration of between $10^{-10}$M and $10^{-4}$M.

15. The method of 12, wherein the auxin is indole-3-acetamide.

16. The method of 12, wherein the auxin is tryptamine.

17. A composition for application to crop plants, the composition comprising a productivity enhancing effective amount of an auxin selected from the group consisting of indole-3-acetamide, tryptamine and a combination thereof.

18. The composition of claim 17, further comprising a surfactant.

19. The composition of claim 17, wherein the auxin is indole-3-acetamide.

20. The composition of claim 17, wherein the auxin is tryptamine.

* * * * *